(12) United States Patent
Kilpadi

(10) Patent No.: US 12,102,511 B2
(45) Date of Patent: Oct. 1, 2024

(54) DRESSING WITH VARIABLE CONTRACTION ZONES

(71) Applicant: Solventum Intellectual Properties Company, Maplewood, MN (US)

(72) Inventor: Deepak V. Kilpadi, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 349 days.

(21) Appl. No.: 17/500,136

(22) Filed: Oct. 13, 2021

(65) Prior Publication Data

US 2022/0031520 A1    Feb. 3, 2022

Related U.S. Application Data

(62) Division of application No. 15/895,851, filed on Feb. 13, 2018, now Pat. No. 11,291,587.

(Continued)

(51) Int. Cl.
*A61M 1/00* (2006.01)
*A61F 13/00* (2024.01)
(Continued)

(52) U.S. Cl.
CPC ........ *A61F 13/05* (2024.01); *A61F 13/00063* (2013.01); *A61F 13/01029* (2024.01);
(Continued)

(58) Field of Classification Search
CPC .......... A61M 1/00; A61M 27/00; A61M 1/90; A61F 13/00; A61F 13/02;
(Continued)

(56) References Cited

U.S. PATENT DOCUMENTS 1,355,846 A    10/1920  Rannells
2,547,758 A     4/1951  Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion for corresponding Application No. PCT/US2018/018054, mailed May 2, 2018.
(Continued)

*Primary Examiner* — Susan S Su
*Assistant Examiner* — Eric Rassavong

(57) ABSTRACT

A manifold for treating a tissue site may include a first side and a second side opposite the first side. The second side of the manifold may be configured to face the tissue site, and to contract a greater amount than the first side of the manifold when exposed to a compressive force. In some illustrative examples, the manifold may be configured to distribute reduced pressure to the tissue site, and to contract when exposed to the reduced pressure. The manifold may be suitable for use with dressing assemblies, treatment systems, and methods for treating a tissue site.

27 Claims, 10 Drawing Sheets

Related U.S. Application Data

(60) Provisional application No. 62/458,916, filed on Feb. 14, 2017.

(51) Int. Cl.

| | | |
|---|---|---|
| *A61F 13/01* | (2024.01) | |
| *A61F 13/05* | (2024.01) | |
| *A61F 13/511* | (2006.01) | |
| *A61F 13/512* | (2006.01) | |
| *A61F 13/514* | (2006.01) | |
| *A61F 13/02* | (2024.01) | |
| *A61M 27/00* | (2006.01) | |

(52) U.S. Cl.
CPC ...... *A61F 13/512* (2013.01); *A61F 13/51456* (2013.01); *A61M 1/90* (2021.05); *A61F 2013/0028* (2013.01); *A61F 2013/5113* (2013.01); *A61F 2013/51139* (2013.01); *A61F 2013/51147* (2013.01)

(58) Field of Classification Search
CPC .......... A61F 13/00029; A61F 13/00068; A61F 13/00063; A61F 13/0216; A61F 13/512; A61F 13/51456; A61F 2013/0028; A61F 2013/5113; A61F 2013/51139; A61F 2013/51147; A61F 13/05; A61F 13/01029
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,569,742 B2 * | 8/2009 | Haggstrom ....... A61F 13/00055 602/41 |
| 7,625,362 B2 | 12/2009 | Boehringer et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,200 B2 * | 10/2012 | Vess ..................... A61M 1/912 604/313 |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,456,928 B2 | 10/2016 | Haggstrom et al. |
| 11,291,587 B2 * | 4/2022 | Kilpadi ............. A61F 13/00068 |

(56) References Cited

U.S. PATENT DOCUMENTS

| | | | |
|---|---|---|---|
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0191196 | A1* | 7/2010 | Heagle ................. B29C 66/232 604/313 |
| 2012/0209226 | A1 | 8/2012 | Simmons et al. |
| 2013/0131564 | A1 | 5/2013 | Locke et al. |
| 2014/0163491 | A1 | 6/2014 | Schuessler et al. |
| 2015/0080788 | A1 | 3/2015 | Blott et al. |
| 2016/0361205 | A1 | 12/2016 | Mumby et al. |

FOREIGN PATENT DOCUMENTS

| | | |
|---|---|---|
| AU | 755496 B2 | 12/2002 |
| AU | 2013270493 B2 | 9/2015 |
| AU | 2014277788 B2 | 11/2016 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 2016195765 A * | 5/2016 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009/146441 A1 | 12/2009 |
| WO | 2012/112204 A1 | 8/2012 |
| WO | 2014/022400 A1 | 2/2014 |

OTHER PUBLICATIONS

Chinese First Office Action Corresponding to Application No. 2018800113631, mailed Mar. 2, 2021.
Japanese Notice of Rejection Corresponding to Application No. 2019543383, mailed Nov. 24, 2021.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

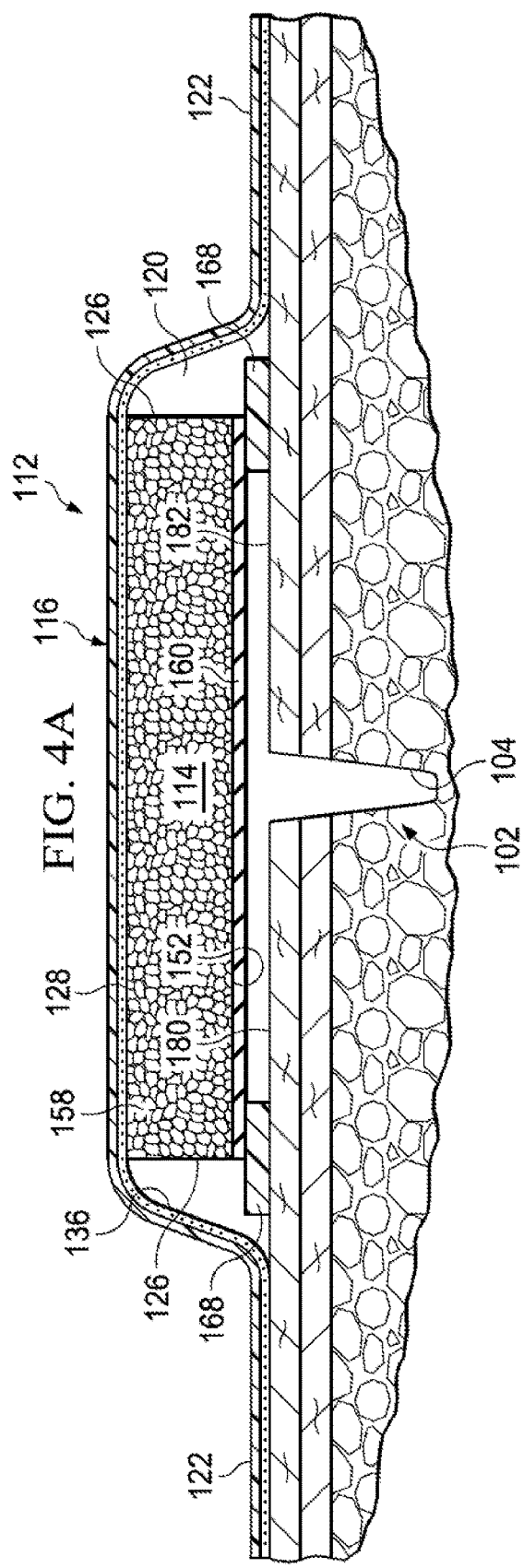
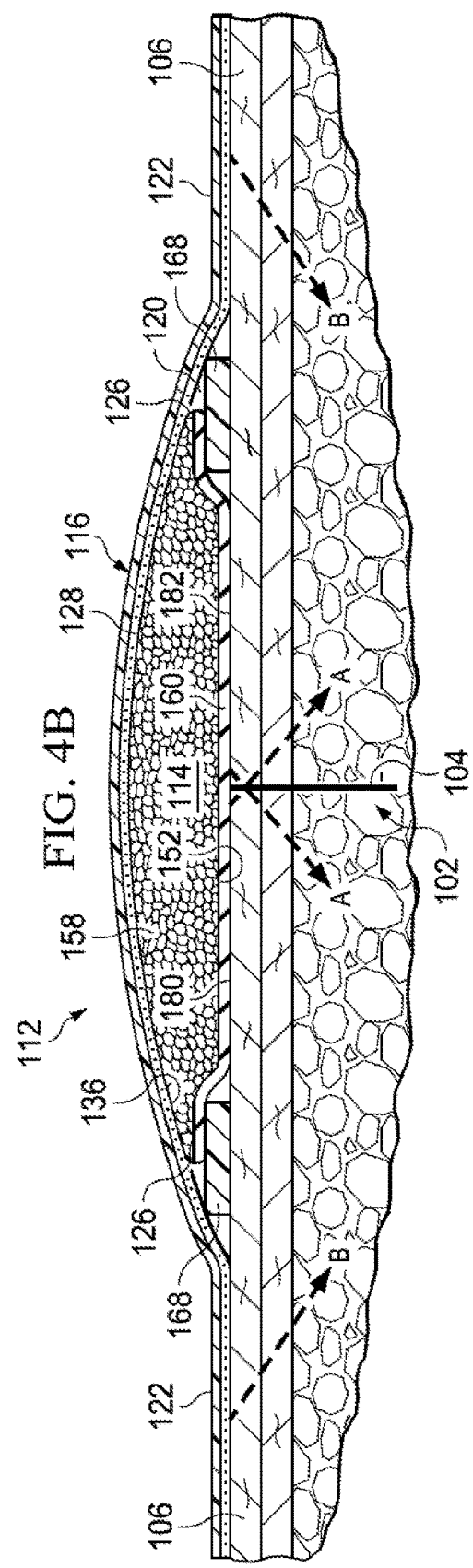

| Time of Measurement | Measurement Location (FIG. 5A) | % DECREASE IN INCISION WIDTH AT THE FOLLOWING LOCATION ALONG THE INCISION IN FIG. 5A | | | | | | | | |
|---|---|---|---|---|---|---|---|---|---|---|
| | | OUTSIDE DRESSING BOLSTER | | BENEATH DRESSING BOLSTER | | | | | OUTSIDE DRESSING BOLSTER | |
| | | 4. END OF INCISION | 3. OUTSIDE DRESSING BOLSTER | 2. DRESSING BOLSTER EDGE | 1. BENEATH DRESSING BOLSTER DISTAL FROM THE CONDUIT INTERFACE END | 0. MIDLINE | -1. BENEATH DRESSING BOLSTER PROXIMAL TO THE CONDUIT INTERFACE END | -2. DRESSING BOLSTER EDGE | -3. OUTSIDE DRESSING BOLSTER | -4. END OF INCISION |
| IMMEDIATELY UPON INITIATION OF OPERATION | BASELINE DRESSING (n=6), MEAN | 18.9 | 32.5 | 38.4 | 49.2 | 53.9 | 47.8 | 43 | 36.2 | 23.5 |
| | BASELINE DRESSING (n=6), SE | 3 | 3.6 | 2.9 | 3.8 | 2.4 | 2.7 | 4 | 4.1 | 4 |
| | DRESSING ASSEMBLY 112 (n=3), MEAN | 25.1 | 56.1 | 80.1 | 83.0 | 79.5 | 74.8 | 73.2 | 57.7 | 31.3 |
| | DRESSING ASSEMBLY 112 (n=3), SE | 0.8 | 2.7 | 0.2 | 0.4 | 0.5 | 1.2 | 1.2 | 2.7 | 5.4 |
| | MEAN RATIO: DRESSING ASSEMBLY 112 / BASELINE DRESSING | 1.3 | 1.7 | 2.1 | 1.7 | 1.5 | 1.6 | 1.7 | 1.6 | 1.3 |
| ONE HOUR POST OF OPERATION INITIATION | BASELINE DRESSING (n=6), MEAN | 20.9 | 37 | 43.9 | 56.8 | 60.6 | 51.2 | 47.4 | 38.4 | 24.5 |
| | BASELINE DRESSING (n=6), SE | 3.1 | 4.2 | 2.8 | 3.8 | 2.6 | 3.2 | 3.5 | 4.1 | 3.6 |
| | DRESSING ASSEMBLY 112 (n=3), MEAN | 31.9 | 62.8 | 86.4 | 86.8 | 82.1 | 79.8 | 78.2 | 70.1 | 42.3 |
| | DRESSING ASSEMBLY 112 (n=3), SE | 2.9 | 1.6 | 2.1 | 0.6 | 0.1 | 0.6 | 1.0 | 0.9 | 3.4 |
| | MEAN RATIO: DRESSING ASSEMBLY 112 / BASELINE DRESSING | 1.5 | 1.7 | 2.0 | 1.5 | 1.4 | 1.6 | 1.7 | 1.8 | 1.7 |

FIG. 5B

DRESSING WITH VARIABLE CONTRACTION ZONES

RELATED APPLICATIONS

This application is a divisional of U.S. patent application Ser. No. 15/895,851, filed Feb. 13, 2018, which claims the benefit under 35 U.S.C. § 119(e), of U.S. Provisional Patent Application No. 62/458,916, filed Feb. 14, 2017, which are incorporated herein by reference for all purposes.

TECHNICAL FIELD

This disclosure relates generally to medical treatment systems and, more particularly, but not by way of limitation, to reduced pressure dressings, systems, and methods for treating a tissue site.

BACKGROUND

Clinical studies and practice have shown that reducing pressure in proximity to a tissue site can augment and accelerate growth of new tissue at the tissue site. The applications of this phenomenon are numerous, but have been proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "reduced-pressure therapy." However, such treatment may also be known by other names including "negative-pressure therapy," "negative-pressure wound therapy," "vacuum therapy," "vacuum-assisted closure," and "topical negative-pressure," for example. Reduced-pressure therapy may provide a number of benefits for both open and incisional wounds, including migration of cells and epithelial and subcutaneous tissues, improved blood flow, and microdeformation of tissue at a tissue site. Together, these benefits can increase development of granulation tissue and reduce healing times. For incision management, the apposition of incisional faces or off-loading of incisional closing devices, such as sutures, may improve outcomes.

Cost and complexity can limit the application of reduced-pressure therapy systems. Development and operation of therapy systems, components, and processes may benefit manufacturers, healthcare providers, and patients.

SUMMARY

In some non-limiting, illustrative examples, a dressing configured to treat a tissue site may include a manifold, a first contraction zone, and a second contraction zone. The manifold may be configured to distribute reduced pressure to the tissue site. The manifold may include a first side, a second side opposite the first side, and a thickness between the first side and the second side. The second side of the manifold may be configured to face the tissue site. The first contraction zone may extend from the first side of the manifold into the thickness of the manifold and toward the second side of the manifold. The first contraction zone may be configured to contract a first amount. The second contraction zone may extend from the first contraction zone into the thickness of the manifold and toward the second side of the manifold. The second contraction zone may be configured to contract a second amount that is greater or different than the first amount when a reduced pressure is applied to the manifold.

In some non-limiting, illustrative examples, a system for treating a tissue site may include a dressing bolster, a comfort layer, and a sealing member. The dressing bolster may include a first side and a second side. The second side of the dressing bolster may be configured to face the tissue site. Further, the dressing bolster may be configured to contract a first amount in a lateral direction relative to the tissue site when exposed to a reduced pressure. The comfort layer may include a first side and a second side. The first side of the comfort layer may be positioned on the second side of the dressing bolster. The comfort layer may be configured to contract a second amount in a lateral direction relative to the tissue site when exposed to the reduced pressure. The second amount of contraction of the comfort layer may be greater than the first amount of contraction of the dressing bolster. The sealing member may be configured to cover the dressing bolster and to create a sealed space relative to the tissue site.

In some non-limiting, illustrative examples, a dressing configured to treat a tissue site may include a manifold and a reinforcing member. The manifold may include a porous material configured to contract and to distribute a reduced pressure to the tissue site. Further, the manifold may include a first side, a second side opposite the first side, and a thickness between the first side and the second side. The second side of the manifold may be configured to face the tissue site. The reinforcing member may be coupled at the first side of the manifold and may be configured to support the first side of the manifold such that the second side of the manifold is configured to contract a greater amount than the first side when the manifold is exposed to the reduced pressure.

In some non-limiting, illustrative examples, a dressing configured to treat a tissue site may include a manifold and a reinforcing member. The manifold may include a foam and may be configured to contract and to distribute a reduced pressure to the tissue site. Further, the manifold may include a first side, a second side opposite the first side, and a thickness between the first side and the second side. The second side of the manifold may be configured to face the tissue site. The reinforcing member may be configured to support the manifold such that the second side of the manifold is configured to contract a greater amount than the first side of the manifold when the manifold is exposed to the reduced pressure.

In some non-limiting, illustrative examples, a dressing configured to treat a tissue site may include a manifold and a reinforcing member. The manifold may be configured to contract and to distribute a reduced pressure to the tissue site. Further, the manifold may include a first side and a second side opposite the first side. The second side may be configured to face the tissue site. The reinforcing member may be configured to support the manifold such that the second side of the manifold is configured to contract a greater amount than the first side of the manifold when the manifold is exposed to the reduced pressure.

In some non-limiting, illustrative examples, a manifold configured to distribute a reduced pressure to a tissue site may include a first side configured to contract a first amount and a second side opposite the first side. The second side of the manifold may be configured to contract a second amount that is greater than the first amount when the manifold is exposed to the reduced pressure.

In some non-limiting, illustrative examples, a dressing configured to treat a tissue site may include a manifold and a reinforcing member. The manifold may include a flexible foam including a plurality of interconnected pores proximate to a first side and a second side of the manifold. The first side of the manifold may be positioned opposite the second side and may be separated from the second side by a thickness of the manifold. The second side may be configured to face the tissue site. The reinforcing member may be configured to support the manifold such that the interconnected pores proximate to the second side of the manifold decrease in size more than the interconnected pores proximate to the first side of the manifold when the manifold is exposed to a reduced pressure.

In some non-limiting, illustrative examples, a method for treating a tissue site may include providing a manifold comprising a first side, a second side opposite the first side, and a thickness between the first side and the second side. Further, the method may include positioning the second side of the manifold proximate to the tissue site, and sealing the manifold at the tissue site with a sealing member to create a sealed space between the sealing member and the tissue site. Further, the method may include contracting at least a portion of the manifold by exposing the manifold to a reduced pressure in the sealed space. Further, the method may include supporting the manifold with a reinforcing member such that the second side of the manifold contracts more than the first side of the manifold.

In some non-limiting, illustrative examples, a method for treating a tissue site may include providing a manifold comprising a first contraction zone and a second contraction zone. Further, the method may include positioning the second contraction zone proximate to the tissue site, and sealing the manifold at the tissue site with a sealing member to create a sealed space between the sealing member and the tissue site. Further, the method may include delivering a reduced pressure from a reduced pressure source to the sealed space, and distributing the reduced pressure to the tissue site through the manifold. Further, the method may include contracting the second contraction zone an amount greater than the first contraction zone.

Other features and advantages of the illustrative embodiments will become apparent with reference to the drawings and detailed description that follow.

BRIEF DESCRIPTION OF THE DRAWINGS

FIG. 4A depicts a cross-section of a portion of an illustrative example of a dressing assembly in a relaxed state prior to operation or application of reduced pressure;

FIG. 4B depicts a cross-section of a portion of an illustrative example of a dressing assembly in a contracted state during operation or application of reduced pressure;

FIG. 5B is a table illustrating an improved decrease in the incision width at the stated times and locations during the test of the dressing assembly compared to a baseline dressing.

DETAILED DESCRIPTION OF ILLUSTRATIVE EMBODIMENTS

In the following detailed description of illustrative embodiments, reference is made to the accompanying drawings that form a part hereof. The illustrative embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. Therefore, the following detailed description is non-limiting, with the scope of the illustrative embodiments being defined by the appended claims.

Figure 1:
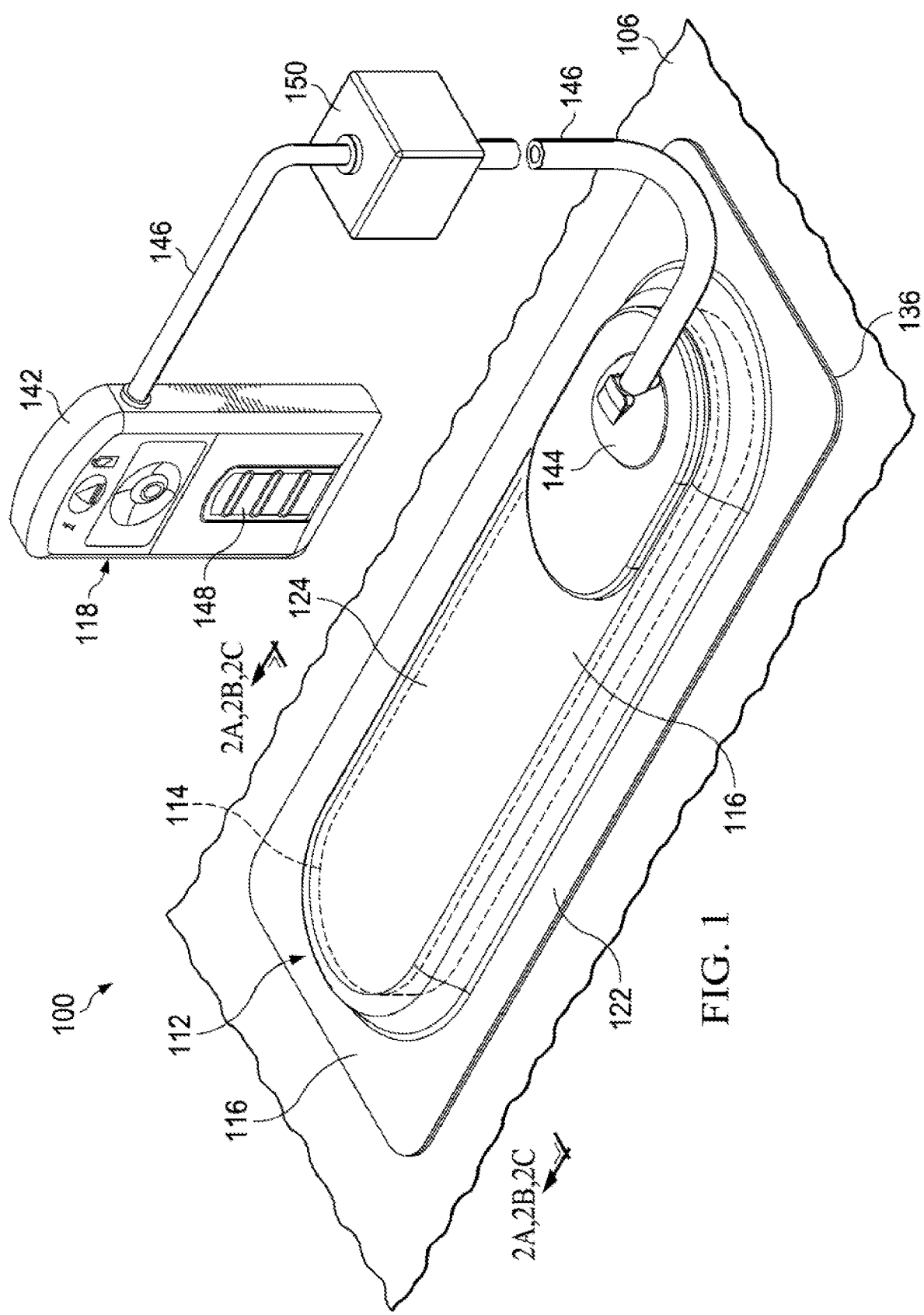
FIG. 1 is a perspective view of an illustrative example of a system and a dressing assembly for treating a tissue site.
Figure 2A:
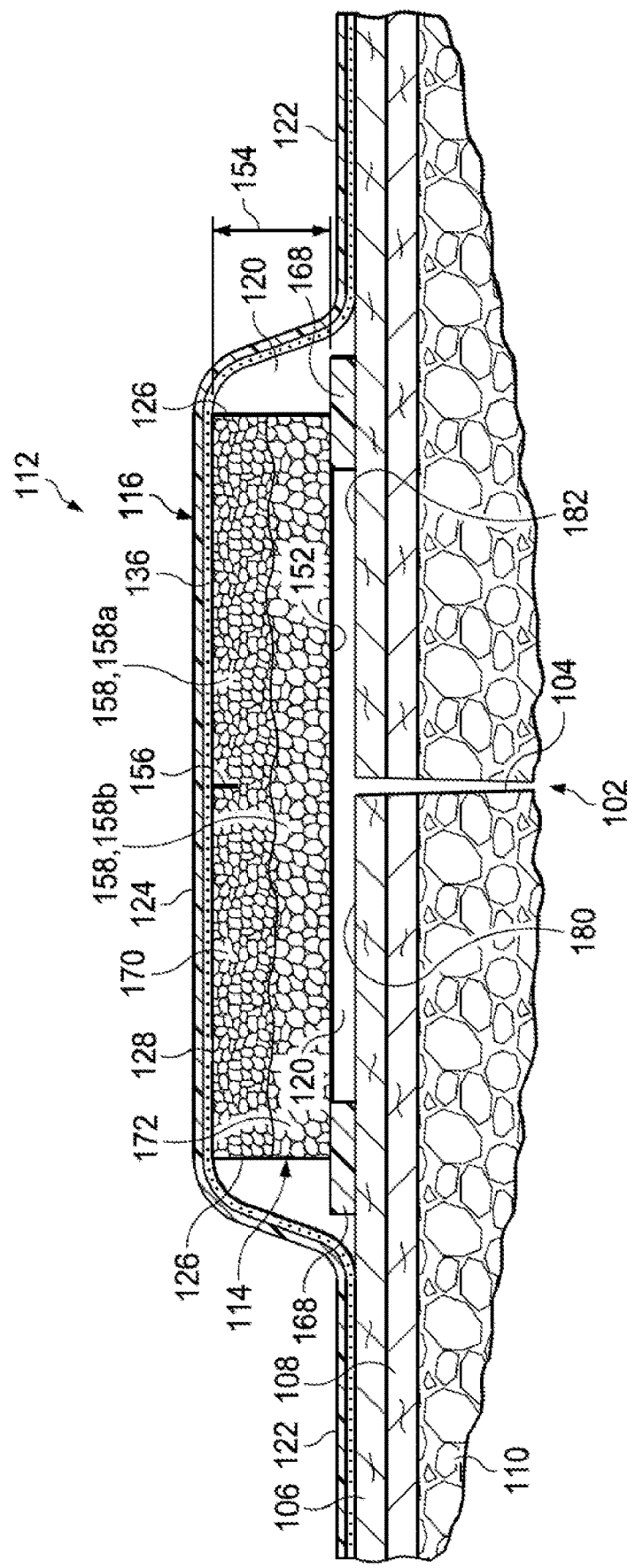
FIG. 2A is a cross-section of a portion of an illustrative example of a dressing assembly taken along line 2A-2A in FIG. 1.

Referring to FIGS. 1 and 2A, presented is an illustrative, non-limiting embodiment of a treatment system 100 for treating a tissue site 102, such as a linear wound or an incision 104. The incision 104 is shown extending through or involving an epidermis 106, a dermis 108, and a subcutaneous tissue 110. The treatment system 100 may also be used with other tissue sites, and may be used with or without reduced pressure.

The treatment system 100 may include a dressing assembly 112. The dressing assembly 112 may include, without limitation, a dressing bolster 114. In some embodiments, the dressing bolster 114 may be a manifold 114. Further, elements of the dressing bolster 114 may be applicable to the manifold 114, and the dressing bolster 114 may be interchangeably referred to herein as the manifold 114. In addition to the dressing assembly 112, the treatment system 100 may include a sealing member 116 and a reduced-pressure subsystem 118. While the treatment system 100 is shown in the context of a reduced-pressure dressing over an incision 104, the treatment system 100 may be used on other tissue sites, including open wounds.

In some embodiments, the sealing member 116 may be a drape 116, and the sealing member 116 or the drape 116 may form part of the dressing assembly 112. The sealing member 116 may be configured to cover the dressing bolster 114 and to create a sealed space 120 relative to the tissue site 102, for example, between the sealing member 116 and the tissue site 102. Further, the sealing member 116 may cover other tissue, such as a portion of the epidermis 106, around or surrounding the tissue site 102 to provide the sealed space 120 between the sealing member 116 and the tissue site 102. The dressing bolster 114 may be positioned in the sealed space 120.

The sealing member 116 may have a periphery 122 and a central region 124. In some embodiments, a portion of the periphery 122 of the sealing member 116 may extend beyond a periphery 126 of the dressing bolster 114 and into direct contact with tissue surrounding the tissue site 102. Further, in some embodiments, the sealing member 116 may be configured to cover at least a portion of a first side 128 of the dressing bolster 114 and to extend beyond the periphery 126 of the dressing bolster 114.

The sealing member 116 may be formed from any material that allows for a fluid seal. A fluid seal may be a seal adequate to maintain reduced pressure at a desired site given the particular reduced pressure source or system involved. The sealing member 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, California; polyether block polyamide copolymer (PEBAX), for example, from Arkema, France; Expopack 2327; or other appropriate material.

The sealing member 116 may be vapor permeable and liquid impermeable, thereby allowing vapor and inhibiting liquids from exiting the sealed space 120. In some embodiments, the sealing member 116 may be a flexible, breathable film, membrane, or sheet having a high moisture vapor transfer rate (MVTR) of, for example, at least about 300 g/m$^2$ per 24 hours. In other embodiments, a low or no vapor transfer drape might be used. The sealing member 116 may comprise a range of medically suitable films having a thickness between about 15 microns (μm) to about 50 microns (μm).

An adhesive 136 may be positioned at least between the periphery 122 of the sealing member 116 and tissue, such as the epidermis 106, surrounding the tissue site 102. In some embodiments, the adhesive 136 may be disposed on a surface of the sealing member 116 adapted to face the tissue site 102. The adhesive 136 may be a medically-acceptable adhesive. The adhesive 136 may also be flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of 15 grams/m$^2$ (gsm) to 70 grams/m$^2$ (gsm). In some embodiments, the adhesive 136 may be continuous layer. In other embodiments, the adhesive 136 may be discontinuous. For example, the adhesive 136 may be a patterned coating on a carrier layer, such as, for example, a side of the sealing member 116 adapted to face the epidermis 106. The discontinuities in the adhesive 136 may also be sized to enhance the Moisture Vapor Transfer Rate (MVTR) of the dressing assembly 112.

The reduced-pressure subsystem 118 may include a reduced-pressure source 142. The reduced-pressure source 142 may provide reduced pressure as a part of the treatment system 100, and may be configured to be coupled in fluid communication with the sealed space 120 to provide reduced pressure to the sealed space 120. For example, the reduced-pressure source 142 may be fluidly coupled to a conduit interface 144 by a delivery conduit 146. An aperture (not shown) may be formed on a portion of the sealing member 116 to allow fluid communication between the sealed space 120 and the reduced-pressure source 142 through the conduit interface 144 and the delivery conduit 146.

As used herein, "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures.

The reduced pressure delivered to the sealed space 120 and the dressing bolster 114 may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

The reduced-pressure source 142 may include a reservoir region 148, or canister region. An interposed membrane filter (not shown), such as a hydrophobic or oleophobic filter, may be interspersed between the reduced-pressure delivery conduit 146 and the reduced-pressure source 142. One or more devices, such as a representative device 150, may be fluidly coupled to the reduced-pressure delivery conduit 146. The representative device 150 may be, for example, another fluid reservoir, a collection member to hold exudates and other fluids removed, a pressure-feedback device, a volume detection system, a blood detection system, an infection detection system, a flow monitoring system, or a temperature monitoring system. Multiple representative devices 150 may be included. One or more of the representative devices 150 may be formed integrally with the reduced-pressure source 142.

The reduced-pressure source 142 may be any device for supplying a reduced pressure, such as a vacuum pump, wall suction, or other source. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The reduced pressure developed by the reduced-pressure source 142 may be delivered through the delivery conduit 146 to the conduit interface 144. The conduit interface 144 may allow the reduced pressure to be delivered through the sealing member 116 to the dressing bolster 114. In some embodiments, the conduit interface 144 may provide fluid communication external to the sealing member 116 without the application of reduced pressure.

Figure 2B:
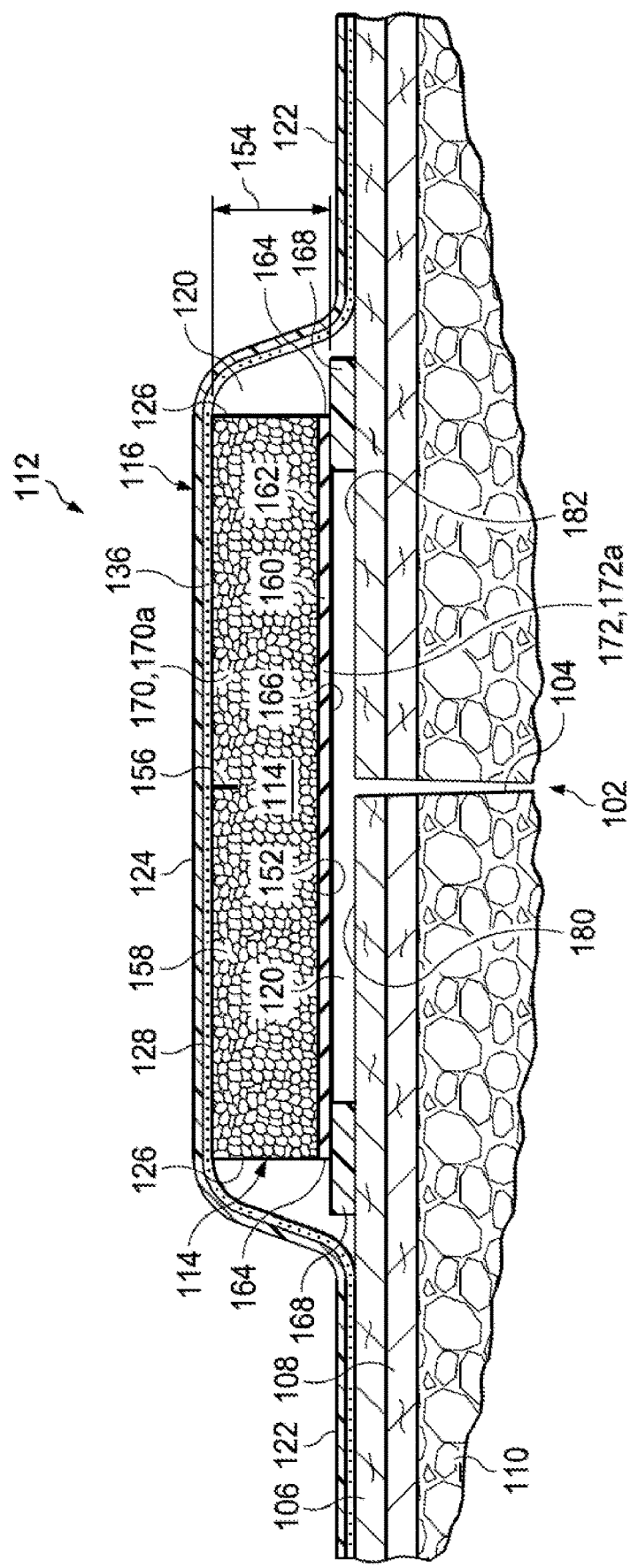
FIG. 2B is a cross-section of a portion of another illustrative example of a dressing assembly taken along line 2B-2B in FIG. 1.
Figure 2C:
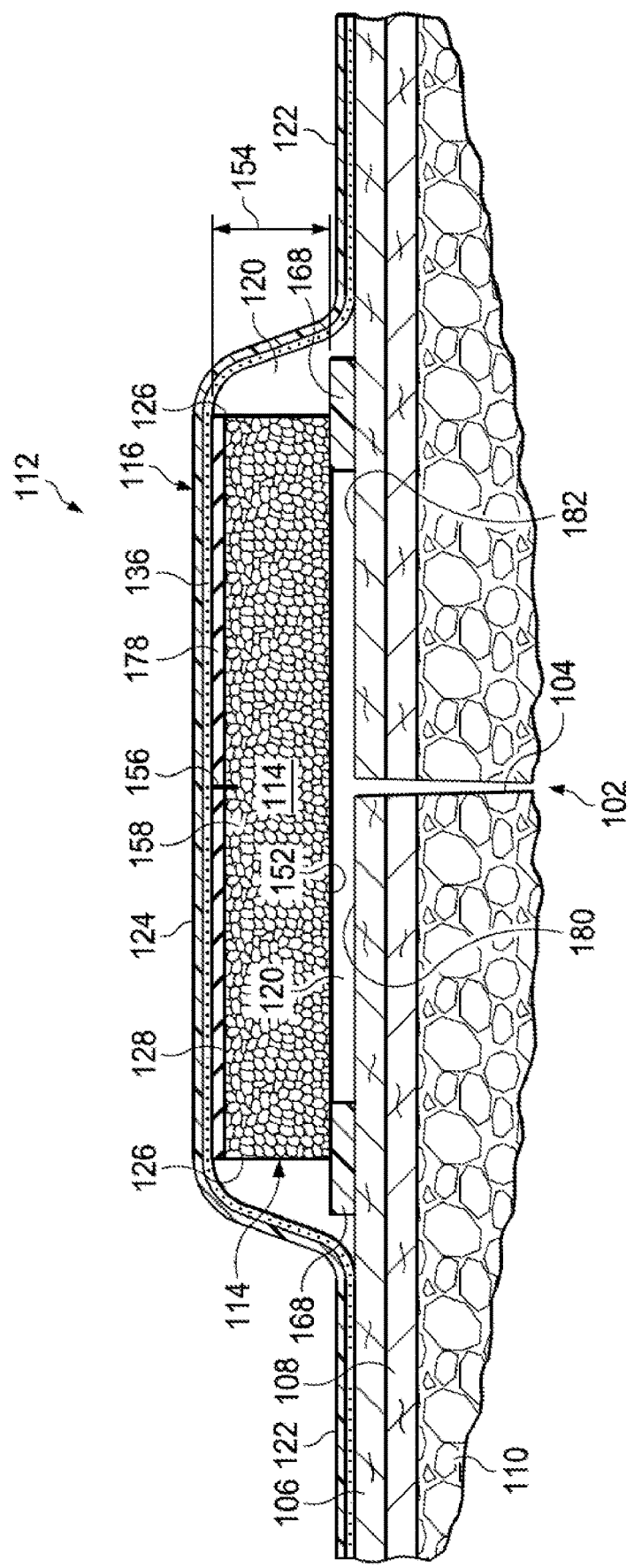
FIG. 2C is a cross-section of a portion of another illustrative example of a dressing assembly taken along line 2C-2C in FIG. 1.

Referring to FIGS. 2A-2C, the dressing bolster 114 may include the first side 128, the periphery 126, and a second side 152. The second side 152 of the dressing bolster 114 may be configured to face the tissue site 102. The first side 128 of the dressing bolster 114 may be opposite the second side 152 such that the first side 128 may be configured to face outward or away from the tissue site 102. The dressing bolster 114 may have a thickness 154 between the first side 128 and the second side 152. The thickness 154 of the dressing bolster 114 may define at least a portion of a thickness of the dressing assembly 112. The periphery 126 of the dressing bolster 114 may define an outer boundary or lateral boundary of the dressing bolster 114 and the first side 128 and the second side 152 of the dressing bolster 114.

In some embodiments, the periphery 126 of the dressing bolster 114 may be an edge 126 of the dressing bolster 114. The edge 126 of the dressing bolster 114 may be a lateral edge positioned orthogonal relative to the second side 152 of the dressing bolster 114. The edge 126 of the dressing bolster 114 may also be a beveled edge or an angled edge. The angled or beveled edge may help distribute shear stress between the dressing bolster 114 and the epidermis 106 of a patient.

In some embodiments, the dressing bolster 114 may include one or more notches, recesses, or cuts, such as a notch 156. For example, the notch 156 may be a lateral or longitudinal cut in the dressing bolster 114 on the first side 128. The notch 156 may enhance the flexibility of the dressing bolster 114. Enhanced flexibility may be particularly useful for application of the dressing assembly 112 over a joint or other area of movement on a patient. The notch 156 may also take various shapes without limitation, such as, for example, hexagons, slits, or squares.

The dressing bolster 114 may be formed from any bolster material or manifold material capable of providing a vacuum space or treatment space. For example, the dressing bolster 114 may be formed from a porous material such as a permeable foam or foam-like material, a flexible foam, a member formed with pathways, a graft, a gauze, or any combination thereof. Reduced pressure applied to the dressing bolster 114 may enhance the permeability of the dressing bolster 114. In some embodiments, the dressing bolster 114 may be formed of or include a wicking material configured to wick fluid or communicate fluid through the dressing bolster 114 with or without the application of reduced pressure.

The term "manifold" as used herein may refer to a substance or structure that may assist in applying or distributing reduced pressure to, delivering fluids to, or removing fluids from a tissue site. A manifold may include a plurality of flow channels or pathways. The plurality of flow channels may be interconnected to improve distribution of fluids provided to and removed from an area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

In some embodiments, the dressing bolster 114 may include a plurality of interconnected pores 158 proximate to the first side 128 and the second side 152 of the dressing bolster 114. In some embodiments, the interconnected pores 158 may have different sizes including one or more small interconnected pores 158a and one or more large interconnected pores 158b. For example, the dressing bolster 114 may be a reticulated, open-cell polyurethane or polyether foam that may be fluid permeable. One such foam material may be a V.A.C.™ GRANUFOAM™ material available from Kinetic Concepts, Inc. (KCI™) of San Antonio, Texas. The reticulated pores of the GRANUFOAM™ material may be helpful in carrying out the manifold function, but as stated above, other materials may be utilized. A material with a higher or lower density than the GRANUFOAM™ material may be desirable in some embodiments. This material may have, for example, a smaller pore size than the GRANUFOAM™ material. Among the many possible materials, the following may be used without limitation: GRANUFOAM™ material, FXI technical foam (www.fxi.com), gauze, a flexible channel-containing member, a graft, and other similar materials. In some embodiments, ionic silver may be added to the material, such as, for example, by a micro bonding process. Other substances, such as antimicrobial agents, may also be added to the material.

In embodiments, the treatment system 100 or the dressing assembly 112 may include a comfort layer 160 having a first side 162, a periphery 164, and a second side 166. In some embodiments, the comfort layer 160 may be an interface layer 160. Further, elements of the comfort layer 160 may be applicable to the interface layer 160, and the comfort layer 160 may be interchangeably referred to herein as the interface layer 160.

The comfort layer 160 may be configured to be positioned between the second side 152 of the dressing bolster 114 and the tissue site 102. The second side 166 of the comfort layer 160 may be configured to face the tissue site 102. The first side 162 of the comfort layer 160 may be opposite the second side 166 of the comfort layer 160 such that the first side 162 may be configured to face outward or away from the tissue site 102. The periphery 164 of the comfort layer 160 may define an outer boundary or lateral boundary of the comfort layer 160 and the first side 162 and the second side 166 of the comfort layer 160. The periphery 164 of the comfort layer 160 may be at least one edge 164 of the comfort layer 160.

The first side 162 of the comfort layer 160 may be positioned on the second side 152 of the dressing bolster 114. In some embodiments, the first side 162 of the comfort layer 160 may be coupled, for example, by a heat bond or other suitable technique to the second side 152 of the dressing bolster 114. In addition to or in lieu of the comfort layer 160 being coupled to the dressing bolster 114, the sealing member 116 may be directly or indirectly coupled to a portion of the comfort layer 160, such as, for example, the periphery 164 of the comfort layer 160. In some embodiments, the periphery 164 of the comfort layer 160 may substantially correspond to, or be substantially aligned with, the periphery 126 of the dressing bolster 114. In some embodiments, the periphery 164 or the at least one edge 164 of the comfort layer 160 may not be coupled to the dressing bolster 114 or may be free of connection to the dressing bolster 114. Further, other portions of the comfort layer 160 or the entire comfort layer 160 may not be coupled to the dressing bolster 114. At least a portion of the comfort layer 160 may be moveable independent of the dressing bolster 114. For example, the comfort layer 160 may be coupled to the dressing bolster 114 lengthwise along a longitudinal axis or midline of the dressing bolster 114, and the at least one edge 164 of the comfort layer 160 may not be coupled to the dressing bolster 114 such that the at least one edge 164 is moveable relative to the dressing bolster 114. The comfort layer 160 may enhance patient comfort when the dressing bolster 114 is adjacent to the epidermis 106 of a patient. For example, in some embodiments, at least a portion of the second side 166 of the comfort layer 160 may be configured to directly contact the tissue site 102.

The comfort layer 160 may be any material suitable for preventing skin irritation and discomfort while allowing fluid transmission through the comfort layer 160. As non-limiting examples, a woven material, an elastic material, a wicking material, a polyester knit textile substrate, a non-woven material, or a fenestrated film may be used. As another non-limiting example, an INTERDRY™ textile material from Milliken Chemical, a division of Milliken & Company, Inc. of Spartanburg, South Carolina, may be used. In some embodiments, the comfort layer 160 may include antimicrobial materials or substances, such as silver.

In some embodiments, the treatment system 100 or the dressing assembly 112 may include an optional interface seal 168. In some embodiments, the interface seal 168 may be a sealing ring 168. Elements of the interface seal 168 may be applicable to the sealing ring 168, and the interface seal 168 may be interchangeably referred to herein as the sealing ring 168. The interface seal 168 may enhance or otherwise provide a fluid seal at or around the tissue site 102, such as the incision 104. For example, a surface of the epidermis 106 may have recesses, cracks, wrinkles, or other discontinuities that may cause leaks. Moreover, folds, buckles, wrinkles, or other discontinuities may form in the sealing member 116 that can cause leaks. The interface seal 168 may help seal any such skin or sealing member discontinuities at or around the tissue site 102. Further, the interface seal 168 may also enhance the ability of the dressing assembly 112 to impart an apposition force to the tissue site 102, for example, for closing the incision 104, or otherwise moving portions of tissue toward one another at the tissue site 102.

The interface seal 168 may function as a two-sided gasket that may provide a seal between the dressing assembly 112 and the tissue site 102 or the epidermis 106. For example, the interface seal 168 may provide a seal between the dressing bolster 114, the comfort layer 160, or the sealing member 116 and the tissue site 102 or the epidermis 106. The interface seal 168 may also absorb perspiration or other fluids from the tissue site 102. Further, the interface seal 168 may distribute shear forces created, for example, by the application of reduced pressure at the interface of the dressing bolster 114 and the tissue site 102 or the epidermis 106.

The interface seal 168 may be configured to be positioned between the dressing bolster 114 and the tissue site 102. For example, the interface seal 168 may be positioned between the second side 152 of the dressing bolster 114 and the tissue site 102. In some embodiments, the interface seal 168 may be coupled to the second side 152 of the dressing bolster 114.

In some embodiments, the interface seal 168 may be positioned at the periphery 126 of the dressing bolster 114, or coupled to the periphery 126 of the dressing bolster 114. Further, the interface seal 168 may be positioned between the dressing bolster 114 and tissue at or around the tissue site 102, such as the epidermis 106. Thus, in some embodiments, at least a portion of the interface seal 168 may be positioned around the periphery 126 of the dressing bolster 114 and a periphery of the tissue site 102. Further, in some embodiments, at least a portion of the interface seal 168 may substantially surround the periphery 126 of the dressing bolster 114 and a periphery of the tissue site 102.

In some embodiments, other layers or elements, such as the comfort layer 160, may be included with the dressing assembly 112 and positioned between the dressing bolster 114 and the interface seal 168. In such embodiments, at least a portion of the second side 152 of the dressing bolster 114 and/or the second side 166 of the comfort layer 160 may be free of the interface seal 168 and configured to be positioned in fluid communication with the tissue site 102.

The interface seal 168 may be formed, as an illustrative example, by applying or bonding sealing material to the dressing bolster 114. The sealing material that may be used for the interface seal 168 may include hydrocolloids, hydrogels, silicone polymers (both crosslinked and uncrosslinked gels), and natural gums (xanthan, guar, cellulose). The sealing material may include other soft polymer gels, such as, for example, those based on polyurethanes, polyolefin gels, and acrylics.

The interface seal 168 may have a durometer, such as a material softness or hardness, between about 20 Shore 00 to about 90 Shore OO. In some embodiments, the durometer of the interface seal 168 may be between about 70 Shore 00 to about 80 Shore OO. Further, the interface seal 168 may have a modulus of elasticity that falls between a modulus of elasticity of the sealing member 116 and a modulus of elasticity of the tissue site 102 and/or the epidermis 106.

The interface seal 168 may have a width between about 10 millimeters to about 30 millimeters. In some embodiments, the width of the interface seal 168 may be about 20 millimeters. The width of the interface seal 168 may be directed, oriented, or adapted for positioning along a surface of the tissue site 102. In some embodiments, the width of the interface seal 168 may extend beyond the edge 126 of the dressing bolster 114 by about 10 millimeters and also overlap the second side 152 of the dressing bolster 114 by about 10 millimeters. Thus, the interface seal 168 may straddle the edge or the periphery 126 of the dressing bolster 114, or otherwise extend beyond the periphery 126 of the dressing bolster 114. In other embodiments (not shown), the dressing bolster 114 may entirely overlap the interface seal 168.

The interface seal 168 may have a thickness between about 0.3 millimeters to about 2.5 millimeters. In some embodiments, the thickness of the interface seal 168 may be between about 0.7 millimeters to about 1.25 millimeters. The thickness of the interface seal 168 may be perpendicular to the width of the interface seal 168 and the tissue site 102. Other dimensions for the interface seal 168 are possible.

The interface seal 168 may be deployed by hand or extruded from an applicator, such as a syringe, prior to application of the dressing assembly 112 to the tissue site 102. Sealing materials suitable for application by extrusion may include water soluble gums such as xanthan, guar, or cellulose, and thick greases, such as silicones. In other embodiments, the interface seal 168 may be bonded in any suitable manner, such as, for example, by a heat bond, to the dressing assembly 112 during manufacture. In some embodiments, the interface seal 168 may have a ring-like or annular shape. In other embodiments, the interface seal 168 may be linear. Further, in some embodiments, the interface seal 168 may comprise one or more discrete members, including linear members, which may be formed into a ring-like or annular shape.

The interface seal 168 may be positioned on or coupled directly to the dressing assembly 112, or coupled with an attachment device, such as an acrylic adhesive, cement, or other coupling device. In some embodiments, the interface seal 168 may be positioned on or coupled to the second side 152 of the dressing bolster 114 and/or to an adjacent layer, such as the second side 166 of the comfort layer 160. Further, in some embodiments, the interface seal 168 may be adapted to be positioned between the comfort layer 160 and the tissue site 102, and/or tissue around the tissue site 102, such as the epidermis 106. Thus, in some embodiments, the comfort layer 160 may be coupled between the dressing bolster 114 and the interface seal 168.

In some embodiments, the interface seal 168 may include an absorbent. For example, the interface seal 168 may be a hydrocolloid comprising an absorbent, such as carboxy methyl cellulose (CMC). The absorbent may permit the interface seal 168 to absorb fluid from the tissue site 102 in addition to enhancing the fluid seal around the tissue site 102. The interface seal 168 including the absorbent may enhance the ability of the dressing assembly 112 to manage and direct fluid away from the tissue site 102 for keeping the tissue site 102 dry. The interface seal 168 may be adapted to be positioned between the dressing assembly 112 and the tissue site 102, as described above, and around or surrounding a circumference, perimeter, or periphery of the tissue site 102.

Relative to the dressing assembly 112, the interface seal 168 may be positioned, for example, around, on, or at the edge or the periphery 126 of the dressing bolster 114 or the edge or the periphery 164 of the comfort layer 160. Further, the interface seal 168 may be positioned around or surrounding a circumference of the dressing bolster 114 or the comfort layer 160. Further, the interface seal 168 may be positioned around at least a portion of the dressing bolster 114 or the comfort layer 160 that is configured to be positioned directly against or in direct contact with the tissue site 102. At least a portion of the dressing bolster 114 or the comfort layer 160 may be exposed and configured to be positioned directly against the tissue site 102 when the interface seal 168 is positioned on the dressing assembly 112. Further, in such embodiments, the interface seal 168 may surround the exposed portion of the dressing bolster 114 or the comfort layer 160.

The absorbent in the interface seal 168 may wick or draw fluid in a lateral direction within the dressing assembly 112, normal to the thickness 154 of the dressing bolster 114, and toward the edge or the periphery 126 of the dressing bolster 114 for absorption in the interface seal 168. Thus, fluid from the tissue site 102 may be wicked or otherwise drawn in a lateral direction along the surface of the tissue site 102 toward the edge or the periphery 126 of the dressing bolster 114 and into the interface seal 168. Further, fluid from the tissue site 102 may also flow through the thickness 154 of the dressing assembly 112 and the dressing bolster 114 at least by operation of the manifold material comprising the dressing bolster 114, described above.

Referring to FIG. 2A, in some illustrative embodiments, the dressing assembly 112 may include a first contraction zone 170 and a second contraction zone 172. The first contraction zone 170 may extend from the first side 128 of the dressing bolster 114 into the thickness 154 of the dressing bolster 114 and toward the second side 152 of the dressing bolster 114. The first contraction zone 170 may be configured to contract a first amount. The first contraction zone 170 may include or form at least a portion of the first side 128 of the dressing bolster 114 such that the first side 128 of the dressing bolster 114 is configured to contract a first amount. In some embodiments, the first contraction zone 170 may have a planar shape extending across or through a width of the dressing bolster 114. The second contraction zone 172 may extend from the first contraction zone 170 into the thickness 154 of the dressing bolster 114 and toward the second side 152 of the dressing bolster 114. In some embodiments, the second contraction zone 172 may have a planar shape extending across or through a width of the dressing bolster 114. The second contraction zone 172 may be configured to contract a second amount that is greater than the first amount when a compressive force is applied to the dressing bolster 114. The second contraction zone 172 may include or form at least a portion of the second side 152 of the dressing bolster 114 such that the second side 152 of the dressing bolster 114 is configured to contract the second amount. In some embodiments, the compressive force applied to the dressing bolster 114 may be generated by a reduced pressure.

The first contraction zone 170 may be configured to contract the first amount and the second contraction zone 172 may be configured to contract the second amount in a direction substantially perpendicular to the thickness 154 of the dressing bolster 114. Further, the first contraction zone 170 may be configured to contract the first amount and the second contraction zone 172 may be configured to contract the second amount in a lateral direction relative to the tissue site 102 and relative to a longitudinal axis or midline of the dressing bolster 114. The first amount of contraction in the first contraction zone 170 and the second amount of contraction in the second contraction zone 172 may reduce a dimension of the dressing bolster 114 in a direction substantially perpendicular to the thickness 154 of the dressing bolster 114.

In some embodiments, the second side 152 of the dressing bolster 114 may be configured to form a concave shape for facing the tissue site 102 when the first contraction zone 170 contracts the first amount and the second contraction zone 172 contracts the second amount. In some embodiments, at least a portion of the second contraction zone 172 may be positioned at the second side 152 of the dressing bolster 114. The second contraction zone 172 may be configured to be positioned between the first contraction zone 170 and the tissue site 102. In some embodiments, the second contraction zone 172 may extend into the thickness 154 of the dressing bolster 114 to a depth greater than a depth of the first contraction zone 170.

In some embodiments, the first contraction zone 170 and the second contraction zone 172 of the dressing bolster 114 or the dressing assembly 112 may include or be formed of multiple layers coupled or positioned as described herein. In other embodiments, the dressing bolster 114 may be a single layer or body configured to contract the first amount in the first contraction zone 170 and the second amount in the second contraction zone 172. For example, in some embodiments, the first contraction zone 170 may have a greater stiffness or rigidity than the second contraction zone 172. In such an embodiment, the first contraction zone 170 and the second contraction zone 172 may each comprise a portion of the manifold or the dressing bolster 114 configured, treated, or modified to have different mechanical properties.

Further, in some embodiments, the first contraction zone 170 and the second contraction zone 172 may comprise a foam having a porosity in the second contraction zone 172 that is greater than a porosity of the foam in the first contraction zone 170. Further, in some embodiments, the foam may have the plurality of interconnected pores 158 in at least one of the first contraction zone 170 and the second contraction zone 172. In some embodiments, the plurality of interconnected pores 158 in the second contraction zone 172 may be larger in size than the plurality of interconnected pores 158 in the first contraction zone 170 of the dressing bolster 114 when the dressing bolster 114 is in a relaxed state. The interconnected pores 158 having a comparatively large size may decrease in size or volume a greater percentage than the interconnected pores 158 having a comparatively small size when exposed to the same compressive force, such as the same amount or level of reduced pressure. The interconnected pores 158 having comparatively large size, such as the large interconnected pores 158b, may have, without limitation, a larger volume, a larger opening, or less resistance to fluid flow compared to the small interconnected pores 158a. Further, a portion of the dressing bolster 114 where the interconnected pores 158 are comparatively large may have a lower density than another portion of the dressing bolster 114 where the interconnected pores 158 are comparatively small.

In some embodiments, the first contraction zone 170 may be configured to contract the first amount and the second contraction zone 172 may be configured to contract the second amount when the dressing bolster 114 is exposed to a reduced pressure. In some embodiments, the first contraction zone 170 may be configured to contract the first amount and the second contraction zone 172 may be configured to contract the second amount when the first contraction zone 170 and the second contraction zone 172 are exposed to equal amounts of a reduced pressure. In some embodiments, the first contraction zone 170 may be configured to contract the first amount and the second contraction zone 172 may be configured to contract the second amount in response to an electrical charge or in response to a mechanical force. Embodiments that use mechanical or electrical components may include, without limitation, springs, solenoids, or other suitable components capable of releasing potential energy or differentially changing length in response to a direct or indirect electrical input.

Referring to FIG. 2B, in some embodiments, the first contraction zone 170 may be a first layer 170a of the dressing assembly 112 and the second contraction zone 172 may be a second layer 172a of the dressing assembly 112. In some embodiments, the first layer 170a may be the dressing bolster 114 and the second layer 172b may be the comfort layer 160. The dressing bolster 114 may be configured to contract a first amount in a lateral direction relative to the tissue site 102 when exposed to a compressive force, such as, for example, a reduced pressure. Further, the comfort layer 160 may be configured to contract a second amount in a lateral direction relative to the tissue site 102 when exposed to the compressive force. The second amount of contraction of the comfort layer 160 may be greater than the first amount of contraction of the dressing bolster 114.

The dressing bolster 114 may be configured to contract the first amount in a direction substantially perpendicular to the thickness 154 of the dressing bolster 114, or in a direction that is lateral, perpendicular, or orthogonal relative to a longitudinal axis or midline of the dressing bolster 114. Further, the comfort layer 160 may be configured to contract the second amount in a direction substantially perpendicular to a thickness of the comfort layer 160 or the thickness 154 of the dressing bolster 114, or in a direction that is lateral, perpendicular, or orthogonal relative to a longitudinal axis or midline of the comfort layer 160 or the dressing bolster 114. The first amount of contraction in the dressing bolster 114 and the second amount of contraction in the comfort layer 160 may reduce a dimension of the dressing bolster 114 and the comfort layer 160 in a direction substantially perpendicular to the thickness 154 of the dressing bolster 114 or a thickness of the comfort layer 160, or in a direction that is lateral, perpendicular, or orthogonal relative to a longitudinal axis or midline of the dressing bolster 114 or the comfort layer 160. In some embodiments, the second side 166 of the comfort layer 160 may be configured to form a concave shape when the dressing bolster 114 contracts the first amount and the comfort layer 160 contracts the second amount.

Referring to FIG. 2C, in some embodiments, the dressing assembly 112 may include a reinforcing member 178 configured to support the manifold 114. The reinforcing member 178 may support the manifold 114 such that the second side 152 of the manifold 114 is configured to contract a greater amount than the first side 128 of the manifold 114 when the manifold 114 is exposed to a compressive force. The compressive force may be, for example, a reduced pressure. In some embodiments, the reinforcing member 178 may be coupled at the first side 128 of the manifold 114 and configured to support the first side 128 of the manifold 114. For example, the reinforcing member 178 may be configured to reduce an amount of contraction at the first side 128 of the manifold 114 relative to the second side 152 of the manifold 114. In some embodiments, the reinforcing member 178 may be configured to preclude contraction at the first side 128 of the manifold 114.

In some embodiments, at least a portion of the manifold 114 may be configured to be positioned between the reinforcing member 178 and the tissue site 102. In some embodiments, the reinforcing member 178 may be positioned to cover at least a portion of the first side 128 of the manifold 114. In some embodiments, the reinforcing member 178 may be positioned across the first side 128 of the manifold 114. In some embodiments, the reinforcing member 178 may be positioned at the periphery 126 of the first side 128 of the manifold 114. In some embodiments, the reinforcing member 178 may be incorporated within at least a portion of the manifold 114. In some embodiments, the reinforcing member 178 may comprise a stiffness, hardness, or rigidity that is greater than a stiffness, hardness, or rigidity of the manifold 114. Although the reinforcing member 178 may have a greater stiffness, hardness, or rigidity than the manifold 114, in some embodiments, the reinforcing member 178 may retain enough flexibility to suitably conform to challenging anatomical surfaces at a particular tissue site.

The first side 128 and the second side 152 of the manifold 114 may be configured to decrease in size in a direction substantially perpendicular to the thickness 154 of the manifold 114 when the manifold 114 is exposed to a reduced pressure. Similarly, the first side 128 and the second side 152 of the manifold 114 may be configured to decrease in size in a lateral direction relative to the tissue site 102. The second side 152 of the manifold 114 may be configured to decrease in size more than the first side 128 of the manifold 114. The manifold 114 may decrease in size when exposed to a compressive force, such as, for example, a reduced pressure.

In some embodiments, the manifold 114 may be flexible and may include the plurality of interconnected pores 158. The plurality of interconnected pores 158 may be configured to decrease in size when the manifold 114 is exposed to a reduced pressure. The plurality of interconnected pores 158 may be positioned proximate to the first side 128 and the second side 152 of the manifold 114. In some embodiments, the plurality of interconnected pores 158 proximate to the second side 152 of the manifold 114 may decrease in size more than the plurality of interconnected pores 158 proximate to the first side 128 of the manifold 114.

For example, in some embodiments, the reinforcing member 178 may be configured to support the interconnected pores 158 proximate the first side 128 of the manifold 114 such that the interconnected pores 158 proximate to the second side 152 decrease in size more than the interconnected pores 158 proximate to the first side 128. For example, the reinforcing member 178 may substantially preclude a deformation or a change in size of at least a portion of the interconnected pores 158 proximate to the first side 152 of the manifold 114. In some embodiments, the reinforcing member 178 may fill at least a portion of the interconnected pores 158 proximate to the first side 128 of the manifold 114. In some embodiments, the reinforcing member 178 may be a coating, strip, layer, or frame of a material suitable for supporting the manifold 114 as described herein.

Figure 3A:
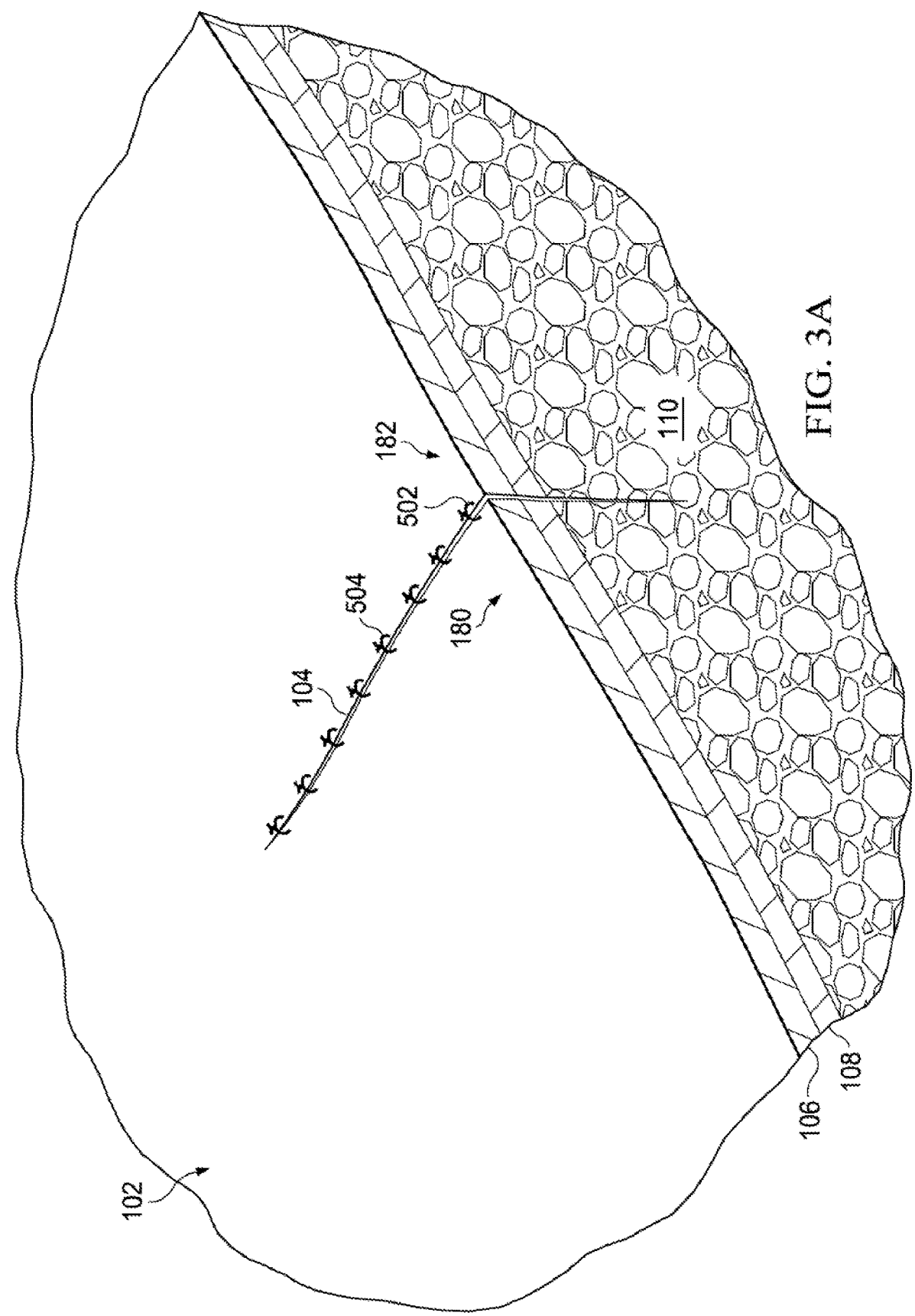
FIGS. 3A-3C are perspective, cross-sectional views of a portion of an illustrative example of a dressing assembly for treating a tissue site being deployed at the tissue site.
Figure 3B:
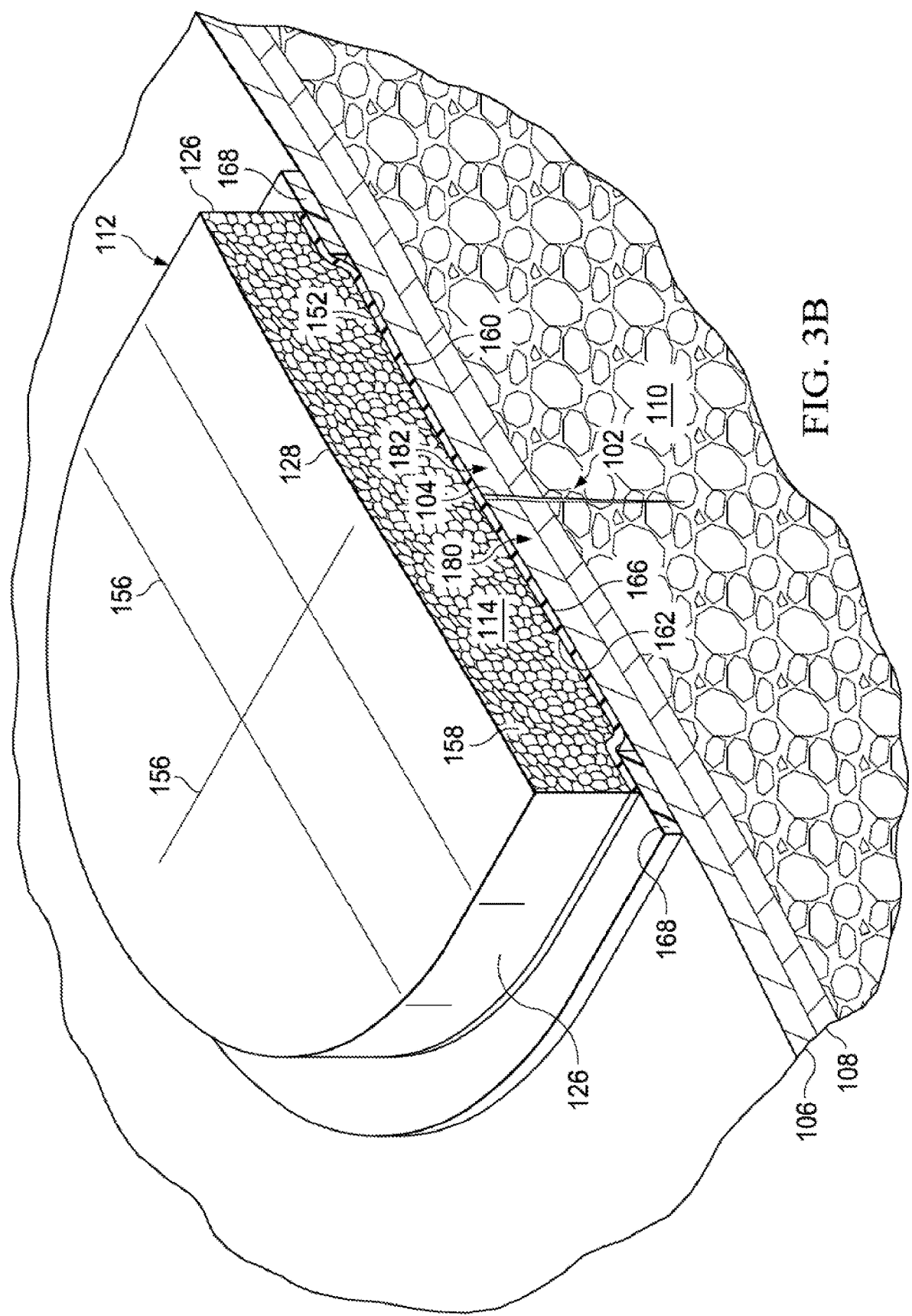
Figure 3C:
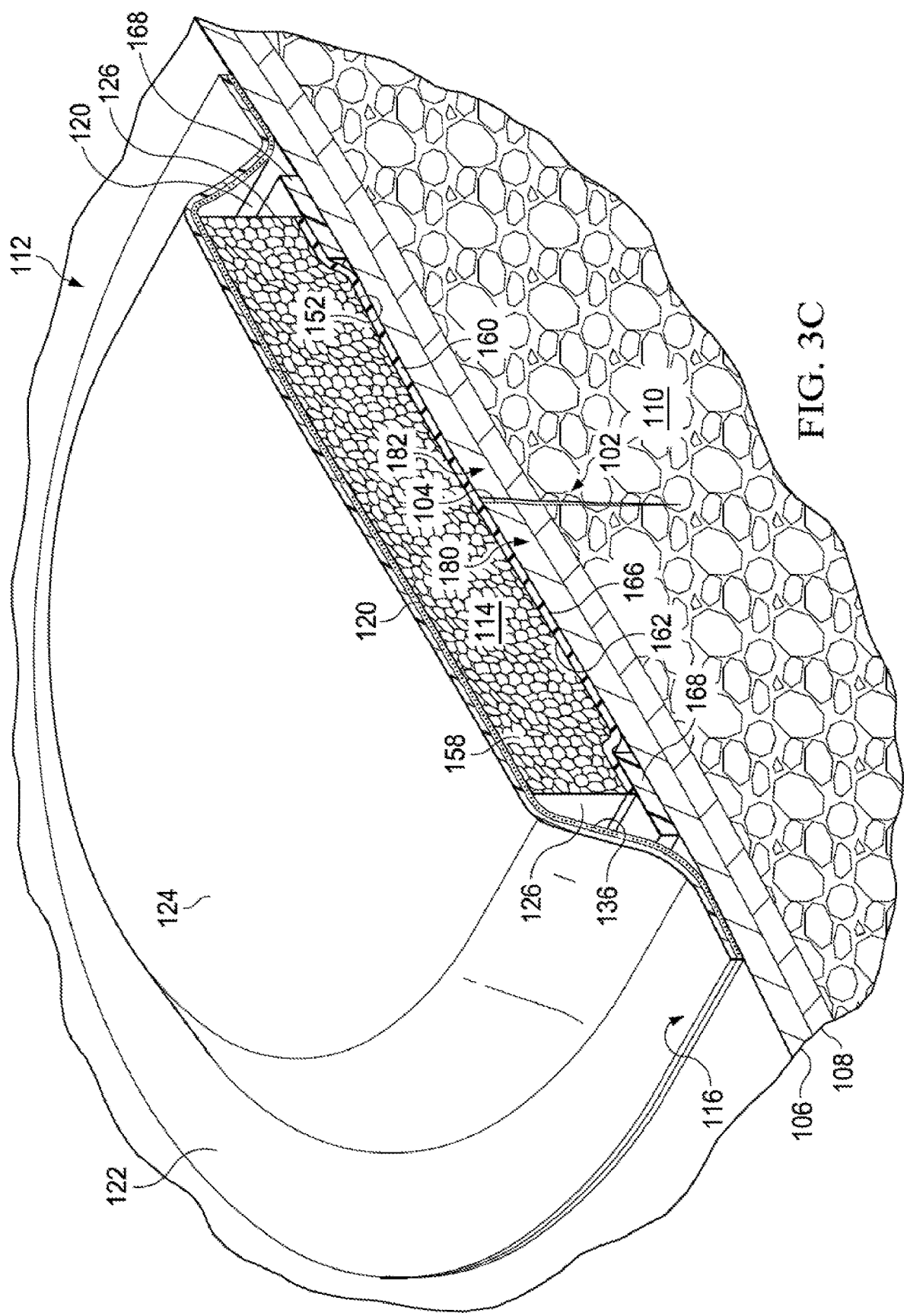

FIGS. 3A-3C provide an illustrative embodiment of a method for assembling the dressing assembly 112 in stages at the tissue site 102, such as the incision 104. In FIG. 3A, a closure device 502, such as, for example, stitches 504, may close the incision 104. Other closure devices 502, such as epoxy or staples may be utilized to close the incision 104. The tissue site 102 may include a first portion 180 and second portion 182. The first portion 180 of the tissue site 102 may be positioned on an opposite side of the incision 104 from the second portion 182 of the tissue site 102.

Referring to FIG. 3B, after the incision 104 is closed or prepared as described above, the dressing assembly 112 may be disposed proximate to the incision 104. For example, the dressing bolster 114 of the dressing assembly 112 may be positioned across the incision 104 between the first portion 180 and the second portion 182 of the tissue site 102. If equipped, the comfort layer 160 may be positioned in contact with the tissue site 102 between the dressing bolster 114 and the tissue site 102. The dressing bolster 114 may be in fluid communication with the tissue site 102 through the comfort layer 160. The interface seal 168 may be positioned at the periphery 126 of the dressing bolster 114 and between the dressing bolster 114 and the tissue site 102. The interface seal 168 may be positioned around a portion of the comfort layer 160 positioned in direct contact with the tissue site 102. The portion of the comfort layer 160 in direct contact with the tissue site 102 may be free of the interface seal 168 such that fluid communication is permitted through the comfort layer 160 to the dressing bolster 114. In other embodiments, elements may be added or omitted as desired. For example, in some embodiments, the comfort layer 160 may be omitted and the dressing bolster 114 may be positioned at the tissue site 102 as described herein.

Referring to FIG. 3C, the sealing member 116 may be disposed over or covering the dressing bolster 114 and a portion of the epidermis 106 to form the sealed space 120 between the sealing member 116 and the incision 104. The sealing member 116 and the adhesive 136 may be deployed together at the tissue site 102 as an assembly or kit. An aperture (not shown) may be formed or preformed in the sealing member 116 to provide fluid communication between the sealed space 120 and the reduced-pressure source 142, such as, for example, through the conduit interface 144 and the delivery conduit 146 previously introduced in FIG. 1.

In operation, reduced pressure may be applied to the tissue site 102, and fluid may be extracted from the tissue site 102 and into the dressing assembly 112. A portion of the fluid from the tissue site 102 may be absorbed into the interface seal 168. Further, the fluid from the tissue site 102 may be wicked or otherwise communicated in a lateral direction within the dressing assembly 112 toward the interface seal 168.

Referring to FIGS. 4A-4B, FIG. 4A depicts an illustrative embodiment of the dressing assembly 112 in a relaxed state positioned at the tissue site 102 prior to operation or application of reduced pressure. FIG. 4B depicts the dressing assembly 112 in a contracted state during operation or application of reduced pressure to the sealed space 120. The dressing assembly 112 of FIGS. 4A-4B is shown with the comfort layer 160. However, any embodiments within the scope of this disclosure, including those that do not use the comfort layer 160, may be suitable, applicable, substituted, or operable in an analogous manner.

During operation in FIG. 4B, the dressing bolster 114 may contract, bend, or curl about a longitudinal axis of the dressing bolster 114 into a convex shape on the first side 128 of the dressing bolster 114 and a concave shape on the second side 152 of the dressing bolster 114 facing the tissue site 102. The longitudinal axis of the dressing bolster 114 may extend into the page in the view shown in FIGS. 4A-4B and be centered along the length of the dressing bolster 114 over the incision 104, for example. With the dressing assembly 112 positioned on the tissue site 102, FIG. 4B does not illustrate the concave shape of the second side 152 of the dressing bolster 114 during operation. However, contraction force vectors (A, B) in FIG. 4B illustrate a direction of a force that may be applied by the dressing assembly 112 during operation. For example, contraction force vector (A) illustrates the direction of the force that may be applied to the tissue site 102 by the second side 152 of the dressing bolster 114. Contraction force vector (B) illustrates the direction of the force that may be applied to the tissue site 102 by the sealing member 116, for example, by the periphery 122 of the sealing member 116 coupled on the epidermis 106 around the tissue site 102. The contraction of the dressing bolster 114 may cause at least one of the edges 126 of the dressing bolster 114 to move toward or closer to one another. The contraction of the dressing bolster 114 may permit the dressing assembly 112 to impart an inward force or an apposition force to the tissue site 102 that may move the first portion 180 of the tissue site 102 toward the second portion 182 of the tissue site 102 as shown by the contraction force vectors (A, B). The movement of the first portion 180 toward or closer to the second portion 182 may provide closure of the incision 104 at the tissue site 102.

In some illustrative embodiments, a method for treating the tissue site 102 may include providing the manifold 114 including the first side 128, the second side 152 opposite the first side 128, and the thickness 154 between the first side 128 and the second side 152. Further, the method may include positioning the second side 152 of the manifold 114 proximate to the tissue site 102. Further, the method may include covering the manifold 114 at the tissue site 102 with a sealing member 116 to create the sealed space 120 between the sealing member 116 and the tissue site 102. Further, the method may include contracting at least a portion of the manifold 114 by exposing the manifold 114 to a reduced pressure in the sealed space 120. Further, the method may include supporting the manifold 114 with a reinforcing member 178 such that the second side 152 of the manifold 114 contracts more than the first side 128 of the manifold 114.

In some embodiments, the manifold 114 may be flexible and may include a plurality of interconnected pores 158 proximate to the first side 128 and the second side 152 of the manifold 114. Contracting at least a portion of the manifold 114 may include decreasing a size of at least a portion of the plurality of interconnected pores 158 such as, for example, by evacuating a fluid from at least a portion of the interconnected pores 158.

In some embodiments, supporting the manifold 114 may include supporting the interconnected pores 158 such that the interconnected pores 158 proximate to the second side 152 of the manifold 114 decrease in size more than the interconnected pores 158 proximate to the first side 128 of the manifold 114. Supporting the manifold 114 may include supporting the first side 128 of the manifold 114 or the interconnected pores 158 proximate to the first side 152 of the manifold 114.

In some illustrative embodiments, a method for treating the tissue site 102 may include providing the manifold 114 including the first contraction zone 170 and the second contraction zone 172. Further, the method may include positioning the second contraction zone 172 proximate to the tissue site 102. Further, the method may include covering the manifold 114 at the tissue site 102 with the sealing member 116 to create the sealed space 120 between the sealing member 116 and the tissue site 102. Further, the method may include delivering a reduced pressure from the reduced pressure source 142 to the sealed space 120. Further, the method may include distributing the reduced pressure to the tissue site 102 through the manifold 114.

Further, the method may include contracting the second contraction zone 172 an amount greater than the first contraction zone 170. For example, the first contraction zone 170 may be configured to contract a first amount and the second contraction zone 172 may be configured to contract a second amount when the reduced pressure is delivered to the sealed space 120. The second amount of contraction may be greater than the first amount of contraction. Contracting the second contraction zone 172 may impart a force on the tissue site 102.

In some embodiments, the method may include positioning the interface layer 160 between the manifold 114 and the tissue site 102. Further, in some embodiments, the second contraction zone 172 may be positioned between the first contraction zone 170 and the tissue site 102. Further, in some embodiments, the manifold 114 may include or be formed of foam.

Figure 5A:
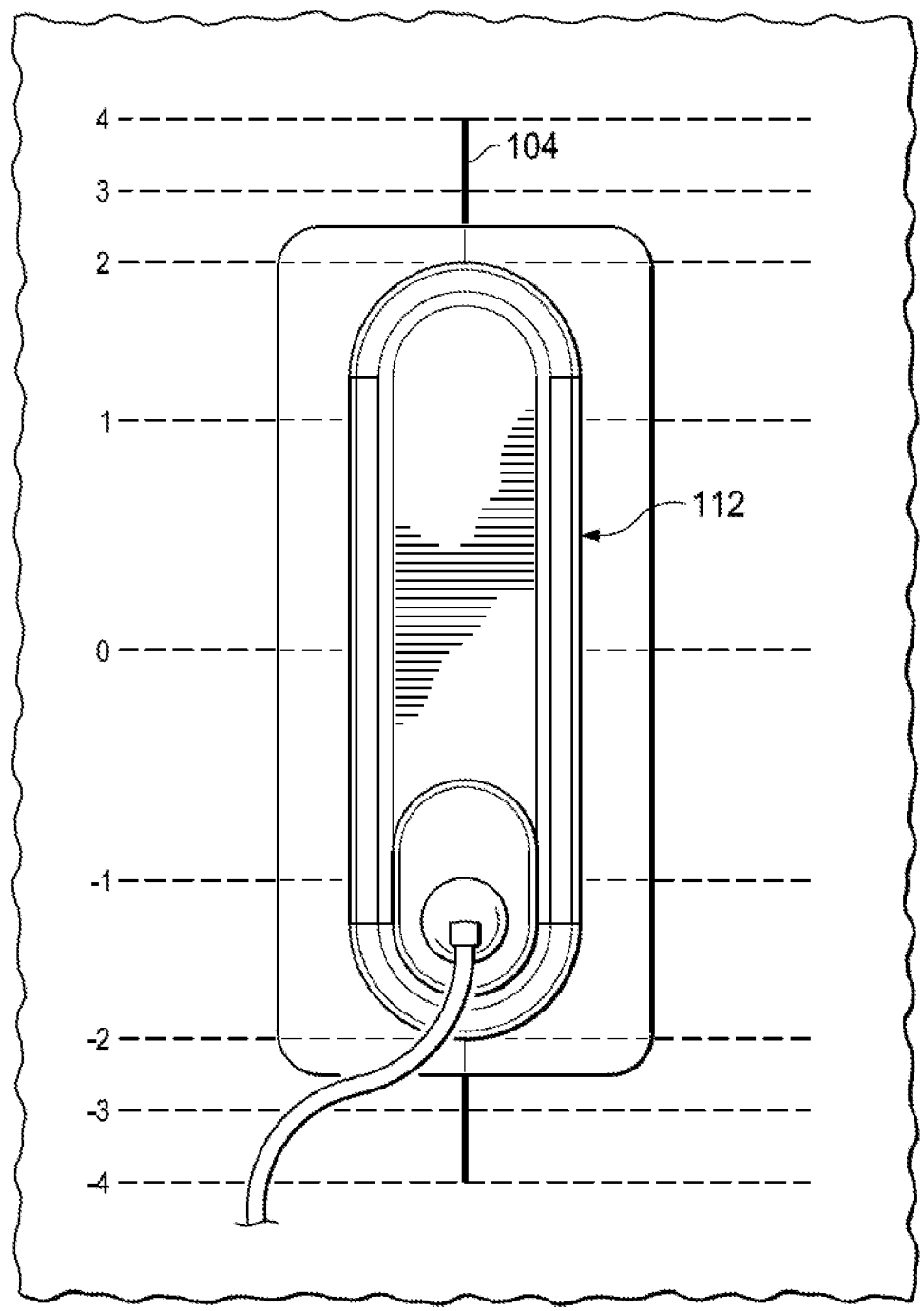
FIG. 5A depicts multiple locations along an incision used to measure a width of the incision during a test of an illustrative example of a dressing assembly.

Referring to FIGS. 5A-5B, provided are testing results for the dressing assembly 112 according to this disclosure. The testing indicates that the dressing assembly 112 may provide a 40% to a 100% improvement in closure of an incision, such as the incision 104, compared to a conventional dressing used to establish a baseline comparison. To replicate the properties of an incision at a tissue site according to this disclosure, a 6 millimeter wide, 36 centimeter long simulated incision was formed in a 3 millimeter thick gel sheet having a thin polymeric film surface. The gel sheet selected for the testing is available under the tradename DERMASOL DS-302.

During the testing, the dressing assembly 112 was applied to the gel sheet in an analogous manner as described herein. The incision width at multiple locations illustrated in FIG. 5A was monitored and measured before operation, immediately upon initiation of operation, and one hour after initiation of operation. FIG. 5A references the measurement locations along the incision 104 relative to the dressing assembly 112 as locations −4, −3, −2, −1, 0, 1, 2, 3, and 4. The same test was performed with a conventional baseline dressing for comparison. The measurement data for the dressing assembly 112 and the baseline dressing are tabulated and compared in FIG. 5B at the stated times and locations. FIG. 5B provides a Mean and Standard Error (SE) for a sample size of six measured data points (n=6) for the baseline dressing and a sample size of three measured data points (n=3) for the dressing assembly 112 at each stated time and location. Also provided is a ratio of the Mean of the sample for the dressing assembly 112 to the Mean of the sample for the baseline dressing. One hour post initiation of operation, FIG. 5B illustrates a Mean Ratio ranging from 1.4 to 2.0, corresponding to a 40% to 100% percent improvement in the closure or decrease of the incision width using the dressing assembly 112.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

I claim:

1. A dressing assembly configured to treat a tissue site, comprising:
   a manifold comprising a porous material configured to contract and to distribute a reduced pressure to the tissue site, the manifold further comprising a first side, a second side opposite the first side, and a thickness between the first side and the second side, the second side configured to face the tissue site; and
   a reinforcing member coupled at the first side of the manifold and configured to support the first side of the manifold such that the second side of the manifold is configured to contract a greater amount than the first side when the manifold is exposed to the reduced pressure, wherein at least a portion of the reinforcing member is positioned at a periphery of the first side of the manifold.

2. The dressing assembly of claim 1, wherein at least a portion of the manifold is configured to be positioned between the reinforcing member and the tissue site.

3. The dressing assembly of claim 1, wherein the reinforcing member is configured to reduce an amount of contraction at the first side of the manifold relative to the second side of the manifold.

4. The dressing assembly of claim 1, wherein the reinforcing member is configured to preclude contraction at the first side of the manifold.

5. The dressing assembly of claim 1, wherein the reinforcing member comprises a stiffness that is greater than a stiffness of the manifold.

6. The dressing assembly of claim 1, wherein the reinforcing member is positioned to cover at least a portion of the first side of the manifold.

7. The dressing assembly of claim 1, wherein the reinforcing member is positioned across the first side of the manifold.

8. The dressing assembly of claim 1, wherein the first side and the second side of the manifold are configured to decrease in size in a direction substantially perpendicular to the thickness of the manifold when the manifold is exposed to the reduced pressure, and wherein the second side of the manifold is configured to decrease in size more than the first side of the manifold.

9. The dressing assembly of claim 1, wherein the first side and the second side of the manifold are configured to decrease in size in a lateral direction relative to the tissue site, and wherein the second side of the manifold is configured to decrease in size more than the first side of the manifold.

10. The dressing assembly of claim 1, wherein the manifold decreases in size when exposed to the reduced pressure.

11. The dressing assembly of claim 1, wherein the manifold is flexible and includes a plurality of interconnected pores configured to decrease in size when the manifold is exposed to the reduced pressure.

12. The dressing assembly of claim 1, wherein the manifold is flexible and includes a plurality of interconnected pores proximate to the first side and the second side of the manifold that are configured to decrease in size when the manifold is exposed to the reduced pressure, and wherein the plurality of interconnected pores proximate to the second side of the manifold decrease in size more than the plurality of interconnected pores proximate to the first side of the manifold.

13. The dressing assembly of claim 1, wherein the manifold is flexible and includes a plurality of interconnected pores proximate to the first side and the second side of the manifold that are configured to decrease in size when the manifold is exposed to the reduced pressure, and wherein the reinforcing member supports the interconnected pores proximate the first side such that the interconnected pores proximate to the second side decrease in size more than the interconnected pores proximate to the first side.

14. The dressing assembly of claim 13, wherein the reinforcing member fills at least a portion of the interconnected pores proximate to the first side of the manifold.

15. The dressing assembly of claim 13, wherein the reinforcing member substantially precludes deformation of at least a portion of the interconnected pores proximate to the first side of the manifold.

16. The dressing assembly of claim 13, wherein the reinforcing member substantially precludes a change in size of at least a portion of the interconnected pores proximate to the first side of the manifold.

17. A treatment system for treating a tissue site comprising the dressing assembly of claim 1, the system further comprising:
- an interface layer configured to be positioned between the second side of the manifold and the tissue site;
- a sealing member configured to cover the manifold and to create a sealed space relative to the tissue site; and
- a reduced-pressure source configured to be coupled in fluid communication with the sealed space and to provide the reduced pressure to the sealed space.

18. A dressing assembly configured to treat a tissue site, comprising:
- a manifold comprising a foam and configured to contract and to distribute a reduced pressure to the tissue site, the manifold further comprising a first side, a second side opposite the first side, and a thickness between the first side and the second side, the second side configured to face the tissue site; and
- a reinforcing member configured to support the manifold such that the second side of the manifold is configured to contract a greater amount than the first side when the manifold is exposed to the reduced pressure, wherein the reinforcing member is incorporated within at least a portion of the manifold.

19. The dressing assembly of claim 18, wherein the reinforcing member is flexible and configured to reduce an amount of contraction at the first side of the manifold relative to the second side of the manifold.

20. The dressing assembly of claim 18, wherein the first side and the second side of the manifold are configured to decrease in size in a direction substantially perpendicular to the thickness of the manifold when the manifold is exposed to the reduced pressure, and wherein the second side of the manifold is configured to decrease in size more than the first side of the manifold.

21. The dressing assembly of claim 18, wherein the manifold is flexible and includes a plurality of interconnected pores proximate to the first side and the second side of the manifold that are configured to decrease in size when the manifold is exposed to the reduced pressure, and wherein the plurality of interconnected pores proximate to the second side of the manifold decrease in size more than the plurality of interconnected pores proximate to the first side of the manifold.

22. The dressing assembly of claim 18, wherein the manifold is flexible and includes a plurality of interconnected pores proximate to the first side and the second side of the manifold that are configured to decrease in size when the manifold is exposed to the reduced pressure, and wherein the reinforcing member supports the interconnected pores proximate the first side such that the interconnected pores proximate to the second side decrease in size more than the interconnected pores proximate to the first side.

23. The dressing assembly of claim 22, wherein the reinforcing member fills at least a portion of the interconnected pores proximate to the first side of the manifold.

24. The dressing assembly of claim 22, wherein the reinforcing member substantially precludes a change in size of at least a portion of the interconnected pores proximate to the first side of the manifold.

25. A treatment system for treating a tissue site comprising the dressing assembly of claim 18, the system further comprising:
- an interface layer configured to be positioned between the second side of the manifold and the tissue site;
- a sealing member configured to cover the manifold and to create a sealed space relative to the tissue site; and
- a reduced-pressure source configured to be coupled in fluid communication with the sealed space and to provide a reduced pressure to the sealed space.

26. A dressing assembly configured to treat a tissue site, comprising:
- a manifold configured to contract and to distribute a reduced pressure to the tissue site, the manifold further comprising a first side and a second side opposite the first side, the second side configured to face the tissue site; and
- a reinforcing member configured to support the manifold such that the second side of the manifold is configured to contract a greater amount than the first side when the manifold is exposed to the reduced pressure, wherein at least a portion of the reinforcing member is positioned at a periphery of the first side of the manifold.

27. A dressing assembly configured to treat a tissue site, comprising:
- a manifold comprising a flexible foam including a plurality of interconnected pores proximate to a first side and a second side of the manifold, the first side positioned opposite the second side and separated from the second side by a thickness of the manifold, the second side configured to face the tissue site; and
- a reinforcing member configured to support the manifold such that the interconnected pores proximate the second side of the manifold decrease in size more than the interconnected pores proximate to the first side of the manifold when the manifold is exposed to a reduced pressure, wherein the reinforcing member fills at least a portion of the interconnected pores proximate to the first side of the manifold.

* * * * *